(12) United States Patent
Yamagishi et al.

(10) Patent No.: US 6,993,176 B2
(45) Date of Patent: Jan. 31, 2006

(54) METHOD AND DEVICE FOR IMAGING LIQUID-FILLED CONTAINER

(75) Inventors: Takahiro Yamagishi, Osaka (JP); Shigeki Tamura, Osaka (JP)

(73) Assignee: Suntory Limited, Osaka (JP)

( * ) Notice: Subject to any disclaimer, the term of this patent is extended or adjusted under 35 U.S.C. 154(b) by 571 days.

(21) Appl. No.: 09/937,988

(22) PCT Filed: Feb. 1, 2001

(86) PCT No.: PCT/JP01/00729

§ 371 (c)(1),
(2), (4) Date: Jan. 2, 2002

(87) PCT Pub. No.: WO01/57504

PCT Pub. Date: Aug. 9, 2001

(65) Prior Publication Data

US 2002/0154809 A1    Oct. 24, 2002

(30) Foreign Application Priority Data

Feb. 3, 2000    (JP) .............................. 2000-026707

(51) Int. Cl.
*G06K 9/00*    (2006.01)

(52) U.S. Cl. .................. 382/142; 382/108; 250/223 B; 356/239.6; 356/428

(58) Field of Classification Search ................ 382/100, 382/108, 141, 142, 149, 152, 153, 199, 254, 382/260, 274–275, 305; 250/223 B, 223 R; 356/246, 426–428, 239.1, 239.4, 237.1, 239.6; 215/12.1, 12.2, 365; 209/522, 523, 524, 209/526; 348/61, 125, 127
See application file for complete search history.

(56) References Cited

U.S. PATENT DOCUMENTS

| 4,026,656 | A |   | 5/1977 | Kusz et al. |
| 4,651,879 | A | * | 3/1987 | Harris et al. ................. 209/523 |
| 4,915,237 | A | * | 4/1990 | Chang et al. ................ 209/524 |

(Continued)

FOREIGN PATENT DOCUMENTS

EP            926486           6/1999

(Continued)

OTHER PUBLICATIONS

Copy of Japanese office action dated Dec. 12, 2004.

*Primary Examiner*—Bhavesh M. Mehta
*Assistant Examiner*—Sheela Chawan
(74) *Attorney, Agent, or Firm*—The Webb Law Firm

(57) ABSTRACT

The present invention is a method and an apparatus for imaging a liquid-filling container in which a light emitting unit is provided for emitting and irradiating light onto the container and a light receiving unit is provided for receiving the light transmitted through the container. The object of the present invention is to provide such a method and an apparatus for imaging a liquid-filling container. This method and apparatus assures reliable detection of the surface of liquid filled in a container or of foreign substance mixed in the liquid or present in the container or the container material not only when the container is transparent, but also when the container is a colored container of a dark color such as black, dark green or dark brown or the container has a frosted surface of when the liquid filled in the container has a dark color. For accomplishing this object, according to the present invention, the light emitting unit emits near infrared light or the light receiving unit receives near infrared light for imaging the container.

24 Claims, 4 Drawing Sheets

U.S. PATENT DOCUMENTS

| | | | |
|---|---|---|---|
| 4,924,107 A * | 5/1990 | Tucker | 250/559.46 |
| 5,095,204 A * | 3/1992 | Novini | 250/223 B |
| 5,523,560 A * | 6/1996 | Manique et al. | 250/223 B |
| 6,067,155 A | 5/2000 | Ringlien | |
| 6,384,421 B1 * | 5/2002 | Gochar, Jr. | 250/559.46 |
| 6,433,338 B1 * | 8/2002 | Nordbryhn et al. | 250/339.12 |

FOREIGN PATENT DOCUMENTS

| | | |
|---|---|---|
| JP | 5180288 | 7/1976 |
| JP | 52-29788 | 3/1977 |
| JP | 5317764 | 2/1978 |
| JP | 54-062885 | 5/1979 |
| JP | 05-099861 | 4/1993 |
| JP | 989805 | 4/1997 |
| JP | 10206214 | 9/1998 |
| JP | 11-503236 | 3/1999 |
| JP | 11248645 | 9/1999 |
| WO | WO 96/31764 | 10/1996 |

* cited by examiner

METHOD AND DEVICE FOR IMAGING LIQUID-FILLED CONTAINER

BACKGROUND OF THE INVENTION

1. Field of the Invention

The present invention relates to a method of imaging a liquid-filling container comprising the steps of emitting and irradiating light onto the container by a light emitting unit, receiving the light transmitted through the container by a light receiving unit and imaging the container based on information about the transmitted light. The invention relates also to an apparatus for carrying out the method above, including the light emitting unit and the light receiving unit.

2. Description of the Prior Art

The imaging of a liquid-filling container noted above is employed in a manufacturing line of various beverages such as soft drinks or alcoholic beverages in order to inspect whether the amount of liquid as the beverage filled in a container made of glass or PET is within a predetermined range or not and/or whether any foreign substance is inadvertently mixed in the beverage filled in the container or is present in the container or mixed in the material forming the container.

According to a conventional method of inspecting beverage by way of imaging of a liquid-filling container, a light emitting unit emits and irradiates a visible light having a wavelength of 400 to 700 nm onto the container to be transmitted through the container and this transmitted light is received by a light receiving unit comprising a CCD camera for imaging of the container, so that the inspection is effected based on the image whether the surface level of the liquid inside the container is within a predetermined range or not, and/or whether any foreign substance is mixed in the beverage or is present in the container or in the container material or not.

Such conventional imaging method as above presents no problem when the container or the liquid/beverage contained therein is transparent or nearly transparent. However, the imaging becomes difficult in case the container is a colored container especially of a dark color such as black, dark green or dark brown or the container has a frosted surface treatment, so that the filled amount of the liquid in the container or absence/presence of any foreign substance in the liquid or in the container or container forming material cannot be detected with high reliability.

Namely, if the container has a dark color such as black, dark green or dark brown, as shown in a graph of FIG. 4 (transmittance for a glass thickness of 3 mm), the transmittance of the visible light becomes extremely low. For this reason, when the visible light emitted from the light emitting unit is received by the light receiving unit, the portion of the visible light travelling outside the container is received substantially as it is or directly by the light receiving unit, so that the amount of received light for this area outside the container is large, whereas the amount of light corresponding to the container is extremely small.

Then, since the inspection of the liquid surface of the liquid filled in the container or of the absence/presence of any foreign substance in the liquid or in the container or the container material is to be effected for such area of extremely limited received light amount, the detection error becomes significant or the detection of the liquid surface or mixed foreign substance per se becomes very difficult. Conventionally, this problem has been coped with by increasing the absolute amount of the visible light to be irradiated onto the container. With this method, however, there remains a significant problem in the detection precision.

Further, even if the container per se does not have such dark color as black, dark green or dark brown, if the liquid filled therein has a dark color, then, the detection of foreign substance in the liquid becomes impossible. Moreover, if fine bubbles generated in association with the filling operation of the liquid are present near the liquid surface, the amount of light transmitted through the bubbles will be small due to the effect of diffused reflection of the light by the bubbles and also the amount of light transmitted through the liquid portion will be limited, so that discrimination therebetween is difficult, thus impeding reliable detection of the liquid surface. Also, if the foreign substance is present near the bubbles, the detection of this mixed substance too can become impossible.

The present invention has addressed to such problems of the prior art as described above. A primary object of the present invention is to provide a method and an apparatus for imaging a liquid-filling container which method and apparatus assure reliable detection of the surface of liquid filled in a container or of foreign substance mixed in the liquid or present in the container or the container material not only when the container is transparent, but also when the container is a colored container of a dark color such as black, dark green or dark brown or the container has a frosted surface or when the liquid filled in the container has a dark color.

SUMMARY OF THE INVENTION

For accomplishing the above object, according to the present invention, as shown in FIGS. 1 and 2 for example, in the method or the apparatus for imaging a liquid-filling container, there are provided a light emitting unit 2 and a light receiving unit 3. The light emitting unit 2 emits and irradiates light onto the container B and the light receiving unit 3 receives the light transmitted through the container for imaging thereof. The light emitting unit 2 emits and irradiates a near infrared light as said light for imaging the container B.

With this characterizing feature, near infrared light is transmitted by the light emitting unit and this transmitted light is received by the light receiving unit for imaging the liquid-filling container. Therefore, the portion of the near infrared light travelling outside the container is received substantially directly by the light receiving unit, so that the amount of received light for the area outside the container is large. However, as may be apparent from the graph in FIG. 4, even if the container has a dark color such as black, dark green or dark brown or if the filled liquid has a dark color or even if the container has a surface frosting treatment, there occurs no significant reduction in the transmittance of the near infrared light through the liquid-filling container. So that, significant reduction in the received light amount for the area corresponding to the liquid-filling container may be avoided advantageously.

Accordingly, various kinds of detection for the area corresponding to this container of the liquid surface level or of any foreign substance mixed into the liquid or present in the container or the container material are made possible. As a result, the various conditions of the liquid-filling container can be reliably detected, regardless of the color of the container or the color of the liquid or regardless of presence/absence of bubbles near the liquid surface.

Incidentally, for imaging a liquid-filling container by irradiating light from the light emitting unit onto the container and receiving the transmitted light by the light receiving unit, according to the present invention, the amount of received light at the area corresponding to the container is positively increased so as to reduce the difference in the received light amounts relative to that of the area corresponding to the outside of the container thereby to improve the detection precision. By irradiating the near infrared light alone or a greater amount of near infrared light component than visible light component of the light, a sufficient amount of near infrared light may be transmitted, depending on the color of the container or the color of the liquid filled therein.

According to the present invention, the light emitting unit 2 comprises a light emitter 2A and a cut filter 5 for filtering light from the light emitter 2A so as to transmit only near infrared light component of the light or a greater amount of near infrared light component than visible light component of the light.

With this characterizing feature, the light emitting unit includes a light emitter and a cut filter for filtering light from the light emitter so as to selectively transmit only near infrared light component of the light or a greater amount of near infrared light component than visible light component of the light. Thus, when e.g. a relatively special near-infrared emitter is employed as the light emitting unit, there is no need of employing any special construction as the light receiving unit. So that, the invention may be embodied, with using a light emitter, a light receiver and a cut filter which are relatively inexpensive.

According to the present invention, as shown in FIGS. 1 and 2 for example, in the method or the apparatus for imaging a liquid-filling container, there are provided a light emitting unit 2 and a light receiving unit 3. The light emitting unit 2 emits and irradiates light onto the container B and the light receiving unit 3 receives the light transmitted through the container for imaging thereof. The light receiving unit 3 receives a near infrared light as said light for imaging the container B.

With this characterizing feature, the liquid-filling container is imaged by receiving near infrared light by the light receiving unit. Therefore, the light receiving unit receives the near infrared light both as the light passing outside the liquid-filling container or the light passing through the liquid-filling container. Hence, there occurs no significant reduction in the received light amount for the area corresponding to the liquid-filling container relative to the received light amount for the area corresponding to the outside of the container even if the container has a dark color such as black, dark green or dark brown, or if the container has a frosted surface treatment or even if the filled liquid has a dark color. Then, various kinds of detection for the area corresponding to this container of the liquid surface level or any foreign substance mixed into the liquid or present in the container or the container material are made possible. As a result, the various conditions of the liquid-filling container can be reliably detected, regardless of the color of the container or the color of the liquid or regardless of presence/absence of bubbles near the liquid surface.

Incidentally, for imaging a liquid-filling container by receiving the transmitted light by the light receiving unit, according to the present invention, the amount of received light received by the light receiving unit at the area corresponding to the container is positively increased so as to reduce the difference in the received light amounts relative to that received by the light receiving unit of the area corresponding to the outside of the container thereby to improve the detection precision. As the light receiving unit receives the near infrared light alone or a greater amount of near infrared light component than visible light component of the light, a sufficient amount of near infrared light may be received, depending on the color of the container or the color of the liquid filled therein.

According to the present invention, as shown in FIG. 2 for example, the light receiving unit 3 comprises a cut filter 5 for filtering the light transmitted through the container so as to transmit only near infrared component of the light or a greater amount of near infrared light component than visible light component of the light and a light receiver 3A for receiving the light transmitted through the cut filter 5.

With this characterizing feature, the light receiving unit includes a cut filter for filtering light the light transmitted through the container so as to transmit only near infrared component of the light or a greater amount of near infrared light component than visible light component of the light and a light receiver for receiving the light transmitted through the cut filter. Therefore, there is no need of employing a special construction as the light receiving unit or no need of employing a relatively special near-infrared light emitter as the light emitting unit. As a result, the invention may be embodied, with using a light emitter, a light receiver and a cut filter which are relatively inexpensive.

According to the present invention, as shown in FIGS. 1 and 2 for example, the light emitting unit 2 and the light receiving unit 3 are disposed so as to enable imaging of a container B which is conveyed one after another along a conveying line 1.

With this characterizing feature, the light emitting unit and the light receiving unit are disposed so as to enable imaging of a container which is conveyed one after another along a conveying line. Therefore, it is possible not only to continuously image a number of liquid-filling containers conveyed one after another, but also to image and detect e.g. the filled condition in each liquid-filling container in a continuous and reliable manner even when containers of various colors or containers containing liquids of various colors are present in a mixed state.

According to the present invention, as shown in FIGS. 1 and 2 for example, there is provided a method or an apparatus for detecting an amount of liquid W filled in the container B.

With this characterizing feature, the method or the apparatus according to the present invention detects an amount of liquid filled in the container. Then, the detection for the area corresponding to this container of the liquid surface level is made possible. As a result, the detection of the liquid level can be effected reliably, regardless of the color of the container or the color of the liquid or regardless of presence/absence of bubbles near the liquid surface.

According to the present invention, as shown FIGS. 1 and 2 for example, there is provided a method or an apparatus for detecting any foreign substance present in the liquid filled in the container.

With this characterizing feature, the method or the apparatus according to the present invention detects any foreign substance present in the liquid filled in the container. Then, the detection for the area corresponding to this container of the foreign substance mixed in the liquid is made possible. As a result, the detection of the foreign substance mixed in the liquid can be effected reliably, regardless of the color of the container or the color of the liquid or regardless of presence/absence of bubbles near the liquid surface.

According to the present invention, as shown in FIGS. 1 and 2 for example, there is provided a method or an apparatus for detecting any foreign substance present in the container B or in a material forming the container B.

With this characterizing feature, the method or the apparatus according to the present invention detects any foreign substance present in the container or in a material forming the container. Then, the detection for the area corresponding to this container of the foreign substance mixed in the container material is made possible. As a result, the detection of the foreign substance mixed in the container material can be effected reliably, regardless of the color of the container or the color of the liquid or regardless of presence/absence of bubbles near the liquid surface.

Incidentally, in the above description, reference marks and numerals were employed for facilitating reference to the accompanying drawings. It is understood that the provision of these marks and numerals is not to limit the invention to the constructions shown in the drawings.

DETAILED DESCRIPTION OF THE PREFERRED EMBODIMENTS

Preferred embodiments of a method and an apparatus relating to the present invention for imaging a liquid-filling container will be described next with reference to the accompanying drawings.

These method and apparatus for imaging a liquid-filling container are for use in e.g., a manufacturing or bottling line of a bottled beverage such as soft drinks or alcoholic beverages, wherein the method or the apparatus is employed for inspecting whether the container or bottle filled with beverage in the foregoing process contains a predetermined filled content of the beverage or not or whether any foreign substance or object other than the beverage may be present inside the filled bottle or not or whether any foreign matter or substance may be present within the material forming the bottle or not. Such manufacturing line, as shown in FIGS. 1 and 2, include a transfer conveyer 1 for conveying a plurality of liquid-filed glass containers or bottles B one after another.

The transfer conveyer 1 conveys, to a predetermined position, each liquid-filling container B which was filled, in the foregoing stage of the process, with beverage W as a liquid by an unillustrated filling device and then fitted atop with a cap C by an unillustrated capping device. Across this conveyer 1 and in opposition to each other, there are disposed a light emitting unit 2 and a light receiving unit 3 together constituting an imaging apparatus.

The light receiving unit 3 is connected with a controller 4, so that light emitted from the light emitting unit 2 is irradiated onto each liquid-filling container B to be transmitted therethrough to be then received by the light receiving unit 3 and based on the information about this received light determination is made by the controller 4 as to whether the amount of the beverage W filled inside each liquid-filling container B is within a predetermined range or not, whether any foreign substance is present within the filled beverage W or not and also whether any foreign substance is present within the material forming the liquid-filling container B or not.

Figure 1:
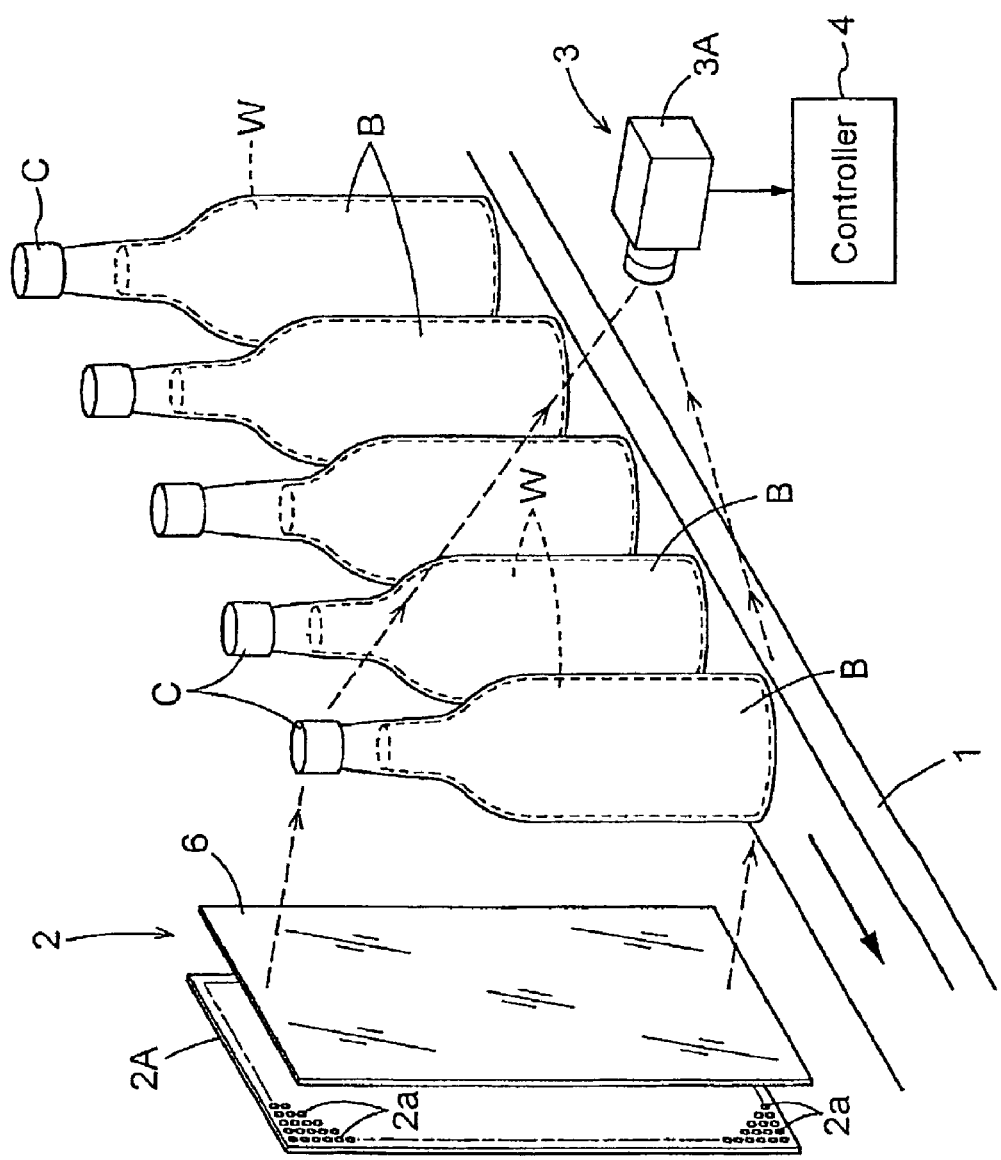
FIG. 1 is a perspective view showing an apparatus for imaging a liquid-filling container relating to a first embodiment of the present invention.
Figure 2:
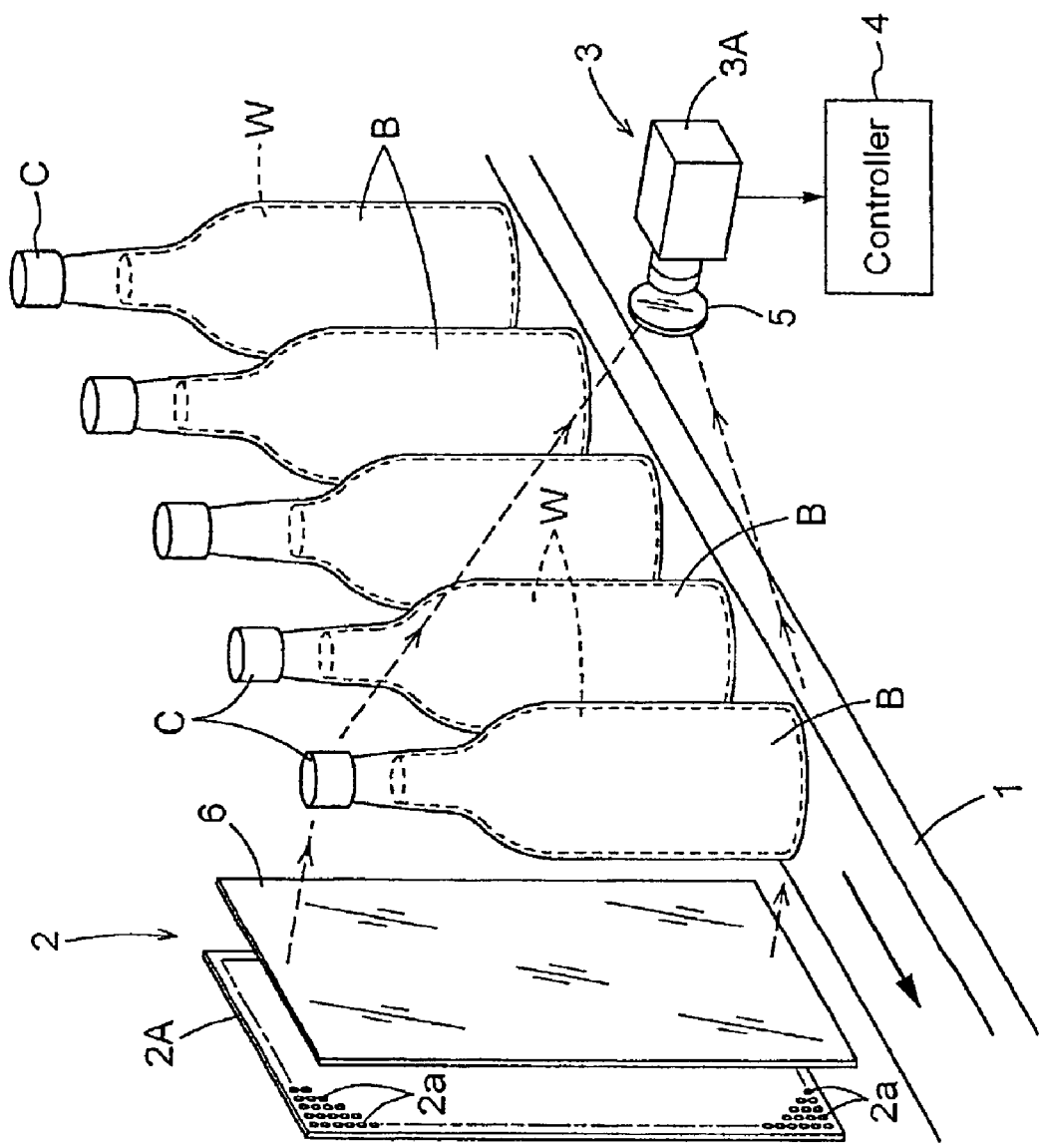
FIG. 2 is a perspective view showing an apparatus for imaging a liquid-filling container relating to a second embodiment of the invention.
Figure 3:
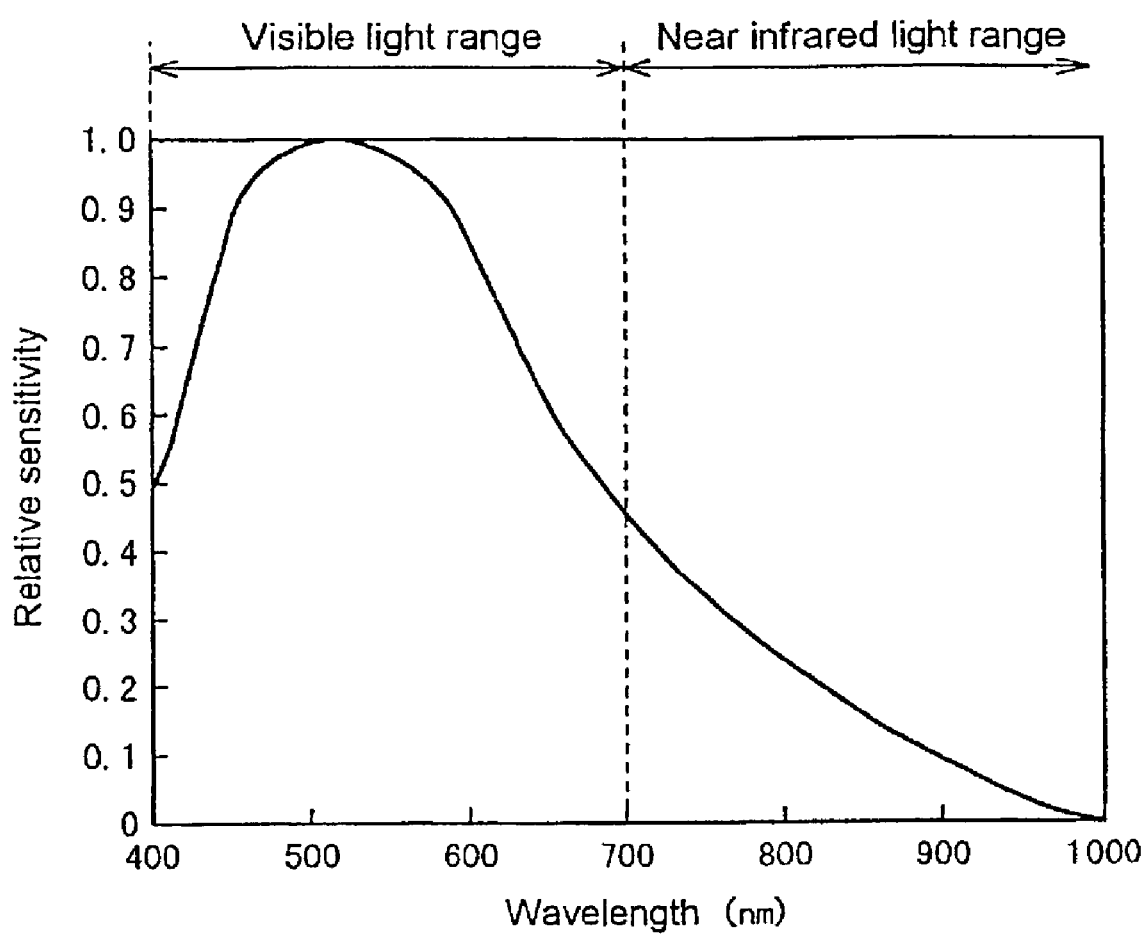
FIG. 3 is a graph showing characteristics of a CCD camera.
Figure 4:
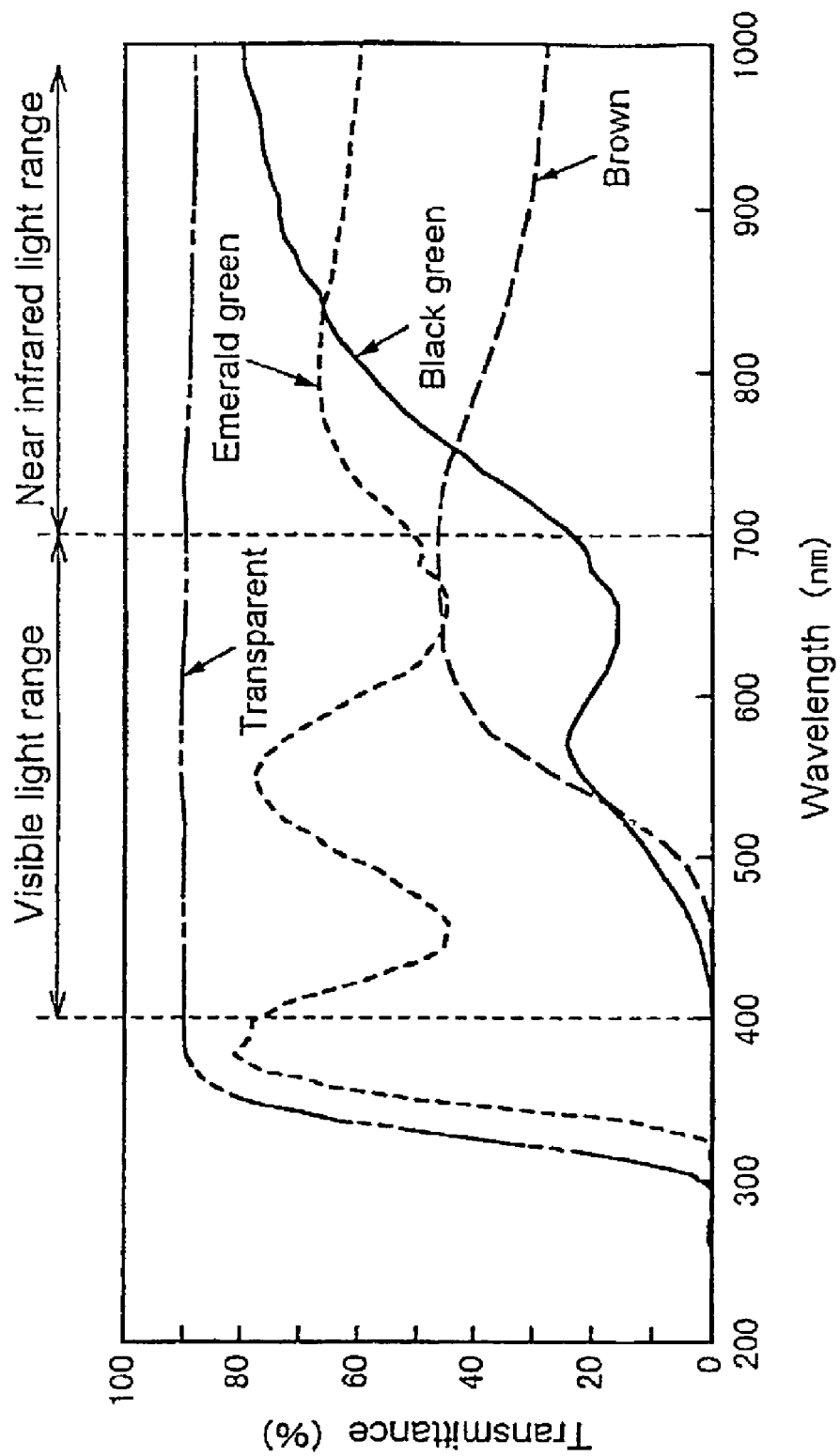
FIG. 4 is a graph showing transmittance of light.

According to a first embodiment of the invention, as shown in FIG. 1, the light emitting unit 2 comprises a light emitter 2A and on the front side of this light emitter 2A there may be provided a diffuser plate 6 formed of an acrylic plate having a milky-white color.

The light emitter 2A may comprise e.g. a plurality of LED 2a arranged in a plate-like form. These plurality of LED 2a emit a light of a predetermined wavelength ranging from 700 nm to 900 nm, preferably from 750 nm to 850 nm, as a near infrared light onto the liquid-filing container B being conveyed on the transport conveyer 1. This irradiated light maybe a light which consists entirely of light component having the wavelength range of 700 nm to 900 nm, preferably 750 nm to 850 nm or which contains such light component as a portion thereof.

The light receiving unit 3 may comprise e.g., a light receiver 3A constituted from a CCD camera. This light receiver 3A is adapted for receiving the near infrared light emitted and irradiated on each liquid-filling container B. Incidentally, such CCD camera exhibits a lower relative sensitivity for the near infrared radiation range than for the visible light range. However, any CCD cameras can be employed as long as their wavelength ranges between 700 nm and 900 nm.

As described above, according to this first embodiment, the light emitting unit 2 emits the near infrared light and after this near infrared light is transmitted through each liquid-filling container B, the transmitted light is received by the light receiving unit 3 comprising the light receiver 3A for its imaging of the container.

Thereafter, the information of this received light is sent to the controller 4 for determination of the filled amount of the beverage W inside each liquid-filling container B, i.e. determination as to whether the liquid surface of the beverage W is within a predetermined level or range or not, determination as to whether any foreign substance is mixed in the beverage W or not and the determination as to whether any foreign substance is mixed within the material forming the container B or not. If any liquid-filling container B is detected to contain more than the predetermined range of beverage W or any foreign substance mixed in the beverage W or in the material forming the container B, then, a certain appropriate measure will be taken, such as automatic removal of this liquid-filling container B away from the conveyer 1 or issuance of an alarm by means of an alarming device.

Incidentally, in the case of this first embodiment shown in FIG. 1, the detection of various conditions is effected on the liquid-filling container B after the container B was filled with beverage W. Alternately, the transfer conveyer 1 may be adapted to convey in succession empty containers B unfilled with the beverage W.

In the case of such alternate construction, the near infrared light emitted from the light emitting unit 2 is transmitted through the empty liquid-filling container B to be received by the light receiver 3; and based on the received transmitted light, determination can be made as to presence/absence of any foreign matter inside the empty container B and within the material forming this container B.

According to a second embodiment of the present invention, as shown in FIG. 2, the light receiving unit 3 includes not only the light receiver 3A comprised of a CCD camera or the like, but also a light-receiver cut filter 5 disposed on the front side of the light receiver 3A.

On the other hand, the light emitting device 2, like the first embodiment described hereinbefore, includes the light emitter 2A comprised of a plurality of LED 2a arranged in a plate-like form and may also include, if necessary, the diffuser plate 6 made of a milky-white acrylic plate. And, the light beam emitted from the number of LED 2a is irradiated onto each liquid-filling container B as being conveyed on the transport conveyer 1.

In the above, after the light is transmitted through each liquid-filling container B, this transmitted light is first filtered by the cut filter 5, so that only or mainly its near infrared component having the wavelength ranging between 700 nm and 900 nm, preferably between 750 nm and 850 nm, is received by the light receiver 3A.

According to this second embodiment, of the light emitted from the light emitting unit 2 and then transmitted through each liquid-filling container B, only or mainly its near infrared light component, i.e. its near infrared component alone or its near infrared component together with a certain less amount of its visible light component is received by the light receiving unit 3, more particularly, the light receiver 3A constituting this light receiving unit 3.

Thereafter, like the foregoing first embodiment, the information about this received light is sent to the controller 4 for determination of the filled amount of the beverage W inside each liquid-filling container B, i.e. determination as to whether the liquid surface of the beverage W is within a predetermined range or not, determination as to whether any foreign substance is mixed in the beverage W or not and the determination as to whether any foreign substance is mixed within the material forming the container B or not. By this process, if any liquid-filling container B is detected to contain more than the predetermined range of beverage W or any foreign substance mixed in the filled beverage W or in the material forming the container B, then, such appropriate measure as exemplified above will be taken.

In addition, in this second embodiment shown in FIG. 2 too, the transfer conveyer 1 may be adapted to convey in succession empty containers B un-filled with the beverage W, instead of filled containers. In such case, of the light emitted from the light emitting unit 2 and then transmitted through each empty container B, only or mainly its near infrared light component (i.e. its near infrared component alone or its near infrared component together with a certain less amount of its visible light component) is received by the light receiving unit 3 for the determination as to presence/absence of any foreign matter inside the liquid-empty container B and within the material forming this container B.

[Other Embodiments]

(1) In the first and second embodiments described above, the single imaging apparatus consisting essentially of the light emitting unit 2 and the light receiving unit 3 is employed for simultaneous detection or determination regarding the presence/absence of any foreign matter inside the liquid-filled or liquid-empty container B and within the material forming this container B. Alternately, the apparatus may be employed for only one detection e.g. the detection of the filled amount of the liquid or beverage W or detection of any foreign substance mixed into the liquid W or into the material forming the container B.

(2) In the first and second embodiments described above, the light receiver 2A is constituted from a number of LED 2a arranged in a plate-like format. In the first embodiment, it is also possible to adapt the light emitting unit 2 per se to emit the near infrared light, by e.g. forming the unit of a near-infrared light emitting diode. Further, in such modified construction of the first embodiment in which the light emitting unit 2 per se emits the near infrared light, the light, the light receiving unit 3 may be comprised of the light receiver 3A and the light-receiver cut filter 5.

Moreover, if the invention is embodied with using a light emitter element or device emitting light of a wide range of wavelength, such as a conventional incandescent electric lamp, a fluorescent lamp, a stroboscopic lamp, etc., and if such light emitting unit additionally includes a diffuser plate on the front of this light emitter, a light-emitter cut filter may be provided in front of or behind it for selective transmission of a predetermined wavelength light component.

(3) In the foregoing embodiments described above, a glass bottle is used as the liquid-filling container B. The invention is not limited thereto. The invention may find utility also for other types of containers or bottles made of other material such as a synthetic resin, exemplified by a PET bottle. Also, in this invention, the type of liquid W is not particularly limited to the beverage. The invention is useful for any other kind of liquid than beverages.

Further, in the foregoing embodiments, the invention is applied in a manufacturing line wherein a plurality of liquid-filling containers B or bottles are conveyed in succession. Instead, the invention may be applied also for detecting the filled amount or mixing of a foreign substance into the liquid or the container forming material for each individual container filled with liquid or empty container.

INDUSTRIAL APPLICABILITY

As described above, the method and apparatus of the invention for imaging a liquid-filled container is suitable, in particular, for a manufacturing line of various beverages such as soft drinks or alcoholic beverages in order to inspect whether the amount of liquid as the beverage filled in the is within a predetermined range or not and/or whether any foreign substance is inadvertently mixed in the beverage filled in the container or present in the container or the material forming the container.

What is claimed is:

1. A method of imaging a liquid-filling container, comprising the steps of:
    emitting and irradiating light onto the container by a light emitting unit,
    receiving the light transmitted through the container by a light reciving unit, and
    imaging inside of the container based on information about the transmitted light,
    wherein said light emitting unit emits and irradiates a near infrared light with a wavelength of 700 to 900 nm as said light for imaging inside of the container, and the container is one of a colored container and a container with a frost surface.

2. The method according to claim 1, wherein said light emitting unit comprises a light emitter and a cut filter for filtering light from the light emitter so as to transmit only near infrared light component of the light or a greater amount of near infrared light component than visible light component of the light.

3. The method according to claim 1, wherein said light emitting unit and said light receiving unit are disposed so as to enable imaging of a container which are conveyed one after another along a conveying line.

4. The method according to claim 1, further including the step of detecting an amount of liquid filled in the container.

5. The method according to claim 1, further including the step of detecting any foreign substance present in the liquid filled in the container.

6. The method according to claim 1, further including the step of detecting any foreign substance present in the container or in a material forming the container.

7. A method of imaging a liquid-filling container, comprising the steps of:
- emitting and irradiating light onto the container by a light emitting unit,
- receiving the light transmitted through the container by a light recieving unit, and
- imaging inside of the container based on information about the transmitted light,
- wherein said light receiving unit receives a near infrared light with a wavelength of 700 to 900 nm as said light for imaging inside of the container, and the container is one of a colored container and a container with a frost surface.

8. The method according to claim 7, wherein said light receiving unit comprises a cut filter for filtering the light transmitted through the containers so as to selectively transmit only near infrared component of the light or a greater amount of near infrared light component than visible light component of the light and a light receiver for receiving the light transmitted through the cut filter.

9. The apparatus according to claim 7, wherein said light emitting unit and said light recieving unit are disposed so as to enable imaging of a container which are conveyed one after another along a conveying line.

10. The method according to claim 7, further including the step of detecting an amount of liquid filled in the container.

11. The method according to claim 7, further including the step of detecting any foreign substance present in the liquid filled in the container.

12. The method according to claim 7, further including the step of detecting any foreign substance present in the container or in a material forming the container.

13. An apparatus for imaging a liquid-filling container comprising:
- a light emitting unit for emitting and irradiating light onto the container, and
- a light receiving unit for receiving the light transmitted through the container,
- wherein said light emitting unit emits and irradiates a near infrared light with a wavelength of 700 to 900 nm as said light for imaging inside of the container, and the container is one of a colored container and a container with a frost surface.

14. The apparatus according to claim 13, wherein said light emitting unit comprises a light emitter and a cut filter for filtering light from the light emitter so as to transmit only near infrared component of the light or a greater amount of near infrared light component of the light than visible light component thereof.

15. The apparatus according to any one of claim 13, wherein said light emitting unit and said light receiving unit are disposed so as to enable imaging of said container which is conveyed one after another along a conveying line.

16. The apparatus according to claim 13, wherein an amount of liquid filled in the container is detected.

17. The apparatus according to claim 13, wherein any foreign substance present in the liquid filled in the container is detected.

18. The apparatus according to claim 13, wherein any foreign substance present in the container or in a material forming the container is detected.

19. An apparatus for imaging a liquid-filling container, comprising:
- a light emitting unit for emitting and irradiating light onto the container, and
- a light receiving unit for receiving the light transmitted through the container,
- wherein said light receiving unit receives a near infrared light with a wavelength of 700 to 900 nm as said light for imaging inside of the container, and the container is one of a colored container and a container with a frost surface.

20. The apparatus according to claim 19, wherein said light receiving unit comprises a cut filter for filtering the light transmitted through the container so as to transmit only near infrared component of the light or a greater amount of near infrared light component than visible light component of the light and a light receiver for receiving the light transmitted through the cut filter.

21. The apparatus according to claim 19, wherein said light emitting unit and said light receiving unit are disposed so as to enable imaging of said container which is conveyed one after another along a conveying line.

22. The apparatus according to claim 19, wherein an amount of liquid filled in the container is detected.

23. The apparatus according to claim 19, wherein any foreign substance present in the liquid filled in the container is detected.

24. The apparatus according to claim 16, wherein any foreign substance present in the container or in a material forming the container is detected.

* * * * *

UNITED STATES PATENT AND TRADEMARK OFFICE
CERTIFICATE OF CORRECTION

PATENT NO. : 6,993,176 B2
DATED : January 31, 2006
INVENTOR(S) : Yamagishi et al.

It is certified that error appears in the above-identified patent and that said Letters Patent is hereby corrected as shown below:

Column 9,
Line 27, "The apparatus" should read -- The method --.

Column 10,
Line 5, "according to any one of claim 13" should read -- according to claim 13 --.
Line 46, "according to claim 16" should read -- according to claim 19 --.

Signed and Sealed this

Sixth Day of June, 2006

JON W. DUDAS
*Director of the United States Patent and Trademark Office*